United States Patent
Ryan et al.

(10) Patent No.: US 10,820,796 B2
(45) Date of Patent: Nov. 3, 2020

(54) PUPIL RADIUS COMPENSATION

(71) Applicant: Tobii AB, Danderyd (SE)

(72) Inventors: Mark Ryan, Danderyd (SE); Simon Johansson, Danderyd (SE); Erik Lindén, Danderyd (SE)

(73) Assignee: Tobii AB, Danderyd (SE)

( * ) Notice: Subject to any disclaimer, the term of this patent is extended or adjusted under 35 U.S.C. 154(b) by 131 days.

(21) Appl. No.: 16/124,776

(22) Filed: Sep. 7, 2018

(65) Prior Publication Data

US 2019/0076014 A1    Mar. 14, 2019

Related U.S. Application Data

(60) Provisional application No. 62/556,116, filed on Sep. 8, 2017.

(51) Int. Cl.
| | |
|---|---|
| *A61B 3/113* | (2006.01) |
| *A61B 3/11* | (2006.01) |
| *A61B 3/00* | (2006.01) |
| *A61B 3/14* | (2006.01) |
| *G06F 3/01* | (2006.01) |
| *G06K 9/00* | (2006.01) |
| *G02B 27/00* | (2006.01) |

(52) U.S. Cl.
CPC ............ *A61B 3/113* (2013.01); *A61B 3/0008* (2013.01); *A61B 3/112* (2013.01); *A61B 3/14* (2013.01); *G06F 3/013* (2013.01); *G06K 9/00604* (2013.01); *A61B 3/0025* (2013.01); *G02B 27/0081* (2013.01)

(58) Field of Classification Search
CPC .......... A61B 3/14; A61B 3/0025; A61B 3/12; A61B 3/102; A61B 3/0008
USPC ........................................... 351/206
See application file for complete search history.

(56) References Cited

U.S. PATENT DOCUMENTS

| | | | |
|---|---|---|---|
| 5,270,748 A | 12/1993 | Katz | |
| 2003/0086057 A1* | 5/2003 | Cleveland | A61B 3/113 351/204 |
| 2003/0123027 A1 | 7/2003 | Amir et al. | |
| 2003/0223037 A1* | 12/2003 | Chernyak | A61B 3/1015 351/209 |
| 2010/0328444 A1 | 12/2010 | Blixt et al. | |
| 2014/0211995 A1* | 7/2014 | Model | G06F 3/013 382/103 |

FOREIGN PATENT DOCUMENTS

| | | |
|---|---|---|
| EP | 3153092 A1 | 4/2017 |
| WO | 2005-046465 A1 | 5/2005 |
| WO | 2013-067230 A1 | 5/2013 |

* cited by examiner

*Primary Examiner* — Mohammed A Hasan
(74) *Attorney, Agent, or Firm* — Samuel Yamron

(57) ABSTRACT

A method is disclosed, comprising obtaining a first angular offset between a first eye direction and a first gaze direction of an eye having a first pupil size, obtaining a second angular offset between a second eye direction and a second gaze direction of the eye having a second pupil size, and forming, based on the first angular offset and the second angular offset, a compensation model describing an estimated angular offset as a function of pupil size. A system and a device comprising a circuitry configured to perform such a method are also disclosed.

17 Claims, 5 Drawing Sheets

PUPIL RADIUS COMPENSATION

CROSS-REFERENCE TO RELATED APPLICATIONS

This application claims priority to and the benefit of U.S. Provisional Patent Application No. 62/556,116, filed Sep. 8, 2017, the entire disclosure of which is incorporated by reference herein for all purposes.

BRIEF SUMMARY OF THE INVENTION

In one embodiment a method is disclosed. The method may include obtaining a first angular offset between a first eye direction and a first gaze direction of an eye having a first pupil size. The method may also include obtaining a second angular offset between a second eye direction and a second gaze direction of the eye having a second pupil size. Thee method may additionally include forming, based on the first angular offset and the second angular offset, a compensation model describing an estimated angular offset as a function of pupil size.

In another embodiment, an eye tracking system is disclosed. The eye tracking system may include circuitry and/or software configured to obtain a first angular offset between a first eye direction and a first gaze direction of an eye having a first pupil size, obtain a second angular offset between a second eye direction and a second gaze direction of the eye having a second pupil size, and form, based on the first angular offset and the second angular offset, a compensation model describing an estimated angular offset as a function of pupil size.

In another embodiment, a device adapted to be worn by a user is disclosed. The device may include at least one illuminator for illuminating an eye of the user, at least one camera for capturing images of the eye, and circuitry/software. The circuitry/software may be configured to obtain a first angular offset between a first eye direction and a first gaze direction of the eye having a first pupil size. The circuitry/software may also be configured to obtain a second angular offset between a second eye direction and a second gaze direction of the eye having a second pupil size. The circuitry/software may additionally be configured to form, based on the first angular offset and the second angular offset, a compensation model describing an estimated angular offset as a function of pupil size.

BRIEF DESCRIPTION OF THE DRAWINGS

Embodiments of the present invention are described in conjunction with the appended figures.

Figure 1:
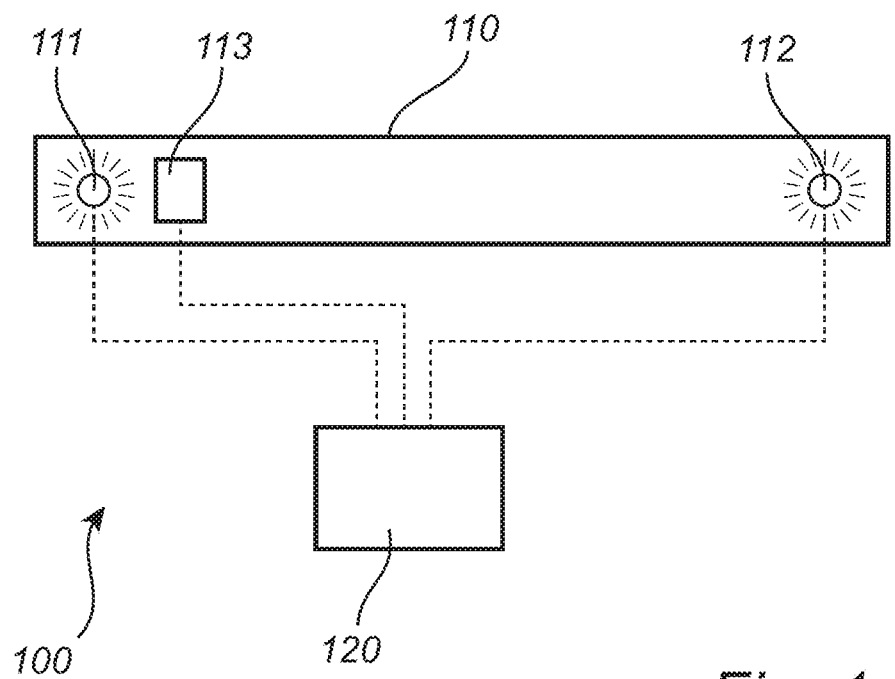
FIG. 1 shows an eye tracking system according to an embodiment of the present invention.

All of the figures are schematic and generally only show parts which are necessary in order to elucidate the respective embodiments, whereas other parts may be omitted or merely suggested.

DETAILED DESCRIPTION OF THE INVENTION

The ensuing description provides exemplary embodiments only, and is not intended to limit the scope, applicability, or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth herein.

For example, any detail discussed with regard to one embodiment may or may not be present in all contemplated versions of that embodiment. Likewise, any detail discussed with regard to one embodiment may or may not be present in all contemplated versions of other embodiments discussed herein. Finally, the absence of discussion of any detail with regard to embodiment herein shall be an implicit recognition that such detail may or may not be present in any version of any embodiment discussed herein.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" or the like includes, but is not limited to transitory and non-transitory, portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

The present disclosure generally relates to the field of eye tracking. In particular, the present disclosure relates to methods and systems for generating and/or using gaze tracking information indicating a gaze direction of an eye.

Several different eye tracking technologies are known in the art. Such technologies may for example be employed to allow a user to indicate a location at visual display by looking at that location. The eye tracking may for example be performed by means of a system that captures images of the user's face and extracts key features from the user's face, such as for example pupil center and glints from illuminators illuminating the user's face. The extracted features may then be employed to determine where at the display the user is looking. Naturally, factors such as accuracy, speed and reliability/robustness of the eye tracking are desirable to achieve a positive user experience. Therefore, several schemes have been proposed for mitigating the negative effects of different types of errors or inaccuracies that may occur in eye tracking systems.

One such example is disclosed in US 2010/0328444 (the entire contents of which are hereby incorporated by reference, for all purposes, as if fully set forth herein), which proposes an eye tracker that includes at least one illuminator for illuminating an eye, at least two cameras for imaging the eye, and a controller. The configuration of the illuminator(s) and cameras is such that at least one camera is non-coaxial with a reference illuminator. The controller is adapted to select camera based on an image quality factor. By performing the camera selection repeatedly, the eye tracking may be based on the one of the two cameras that yields the best quality metric. In this way, the eye tracking becomes less vulnerable to disturbances, such as sight-obscuring objects.

Although such technologies may provide a more robust and accurate tracking of the eye, there is still a need for improved eye tracking systems and methods.

An objective of the present disclosure is to provide a technology allowing for eye tracking methods, systems and devices having an improved performance. Additional and alternative objects may be understood from the following.

The present disclosure relates to a technology in which an angular offset between eye direction and gaze direction of a user's eye may be obtained, e.g. during a calibration procedure, and employed for subsequent tracking of movements of the eye. The eye direction may be understood as a three-dimensional vector defined by the relative position of the cornea and the pupil of the eye. The eye direction may thus be understood as the relative direction of the eye in space, and may also be referred to as the optical axis of the eye. The gaze direction, on the other hand, may be understood as the visual axis, or line of sight, represented by a three-dimensional vector defined by the point of gaze of the user and the foveal region of the eye. The gaze direction often deviates from the eye direction by an angular offset that may be eye/subject dependent. Therefore, the angular offset may be determined in e.g. a calibration procedure, in which the user views an animated or static calibration pattern having one or several points (i.e., points of gaze) having a known position or a movement trajectory, while the eye direction is measured by observing for example pupil location and glints from illuminators illuminating the user's face the. The measured eye direction can then be compared to the known gaze direction of the user viewing for example a calibration pattern.

Hence, according to a first aspect, there is provided method comprising the steps of obtaining a first angular offset between a first eye direction and a first gaze direction of an eye having a first pupil size, obtaining a second angular offset between a second eye direction and a second gaze direction of the eye having a second pupil size, and forming, based on the first angular offset and the second angular offset, a compensation model describing an estimated angular offset as a function of pupil size.

According to a second aspect, there is provided a system comprising a circuitry configured to perform the method steps according to the first aspect, i.e., to obtain a first angular offset between a first eye direction and a first gaze direction of an eye having a first pupil size, obtain a second angular offset between a second eye direction and a second gaze direction of the eye having a second pupil size, and form, based on the first angular offset and the second angular offset, a compensation model describing an estimated angular offset as a function of pupil size.

The eye direction may be determined by observing the pupil position, such as the location of an estimated pupil center, in relation to an estimated cornea center. These two positions give the eye direction, or visual axis of the eye. A problem exists, however, in that as the iris dilates and constricts, the pupil typically does not open and close completely concentrically about a fixed point in the eye. In other words, the estimated pupil center position may vary with the pupil size in a way that may be eye or subject dependent. As a result, the estimated eye direction and hence its angular offset to the gaze direction may vary with the size of the pupil. Thus, by forming a compensation model describing the estimated angular offset as a function of pupil size, this effect can be compensated for and the accuracy of the eye tracking improved. In particular, this allows for a gaze tracking that is less sensitive to errors and deviations associated with varying lighting conditions that affects the pupil size. The present inventive concept is therefore of particular interest in applications utilizing for example dynamic display brightness (such as e.g. virtual reality applications) or used in ambient lighting (such as e.g. augmented reality applications).

In the above, the compensation model is based on two measured points, i.e., the first angular offset for the first pupil size, and the second angular offset for the second pupil size. It is however appreciated that this is merely an illustrating example, and that the model just as well may be based on data sets comprising two or more measured points. Further, the compensation model may be updated in subsequent calibration processes, taking into account further angular offsets associated with further pupil sizes. Thus, the present disclosure is not limited to a compensation model formed from two data points or formed at a specific point in time. It may as well be a dynamic model that is updated whenever relevant data is acquired, or upon request by a user or provider.

As already mentioned, the compensation model may be used for improving the gaze tracking by dynamically adapting the calculation of the gaze direction to the actual size of the pupil. Hence, according to an embodiment, the method may further comprise obtaining a third eye direction of the eye having a third pupil size, and determining, based on the compensation model, an estimated angular offset associated with the third pupil size. This angular offset may then be employed for determining, based on the third eye direction, a third gaze direction of the eye having the third pupil size. The present embodiment may thus represent the method or system during operation, i.e., when the eye tracking technology is employed for determining the gaze direction of the user. In that case, the above described steps of obtaining the third eye direction and determining the gaze direction based on the angular offset of the particular pupil size, may be performed repeatedly during the operation.

According to some embodiments, the first eye direction and the first pupil size may be obtained from a first image of the eye having the first pupil size, wherein the second eye direction and the second pupil size may be obtained from a second image of the eye having the second pupil size. In one embodiment, the method may include the steps of acquiring the first image and the second image of the eye. These images may e.g. be obtained from one or several image sensors included in the system, or from elsewhere. The pupil size in the respective images may be determined as the size of the pupil as represented in the image, or as the actual pupil size. Using the actual pupil size is advantageous in that the size may not depend on the distance between the eye and the image sensor, or camera.

According to an embodiment, the first image may be acquired at a first illumination intensity and the second image at a second illumination intensity, differing from the first illumination intensity. The illumination intensity may for example be actively changed when capturing the second image, for example by changing a display brightness, so as to obtain calibration data for different pupil sizes. Thus, the change in illumination intensity may be included as an active step in a calibration process. In another example, the capturing of the second image may be triggered by a predetermined change in the illumination intensity, i.e., when a predetermined change in illumination intensity is detected, or when a predetermined change in pupil size is detected.

According to an embodiment, the eye direction may be determined based on a relative position between an estimated cornea center and an estimated pupil center. This may for example be achieved by illuminating the eye with an illuminator, such as e.g. an infrared or near-infrared illuminator, causing at least two reflections or glints on the eye. A two-dimensional image may then be captured and analyzed to determine the positions in the image in which the reflections are located. If the cornea is assumed to have a spherical shape, i.e., such that the observed surface portion of the cornea may be approximated by a segment of a sphere, the positions of the reflections can be used to derive an estimated cornea sphere center in the eye. The estimated pupil center may be derived from an image of the eye, for example based on image analysis in which the boundary between the iris and the pupil. The pupil, as identified in the image, may be projected onto a model of the cornea so as to determine an estimated center of the pupil in the actual eye. The first eye direction and the second eye direction may be then be determined based on the location of the estimated cornea sphere center and the location of an estimated pupil center.

The gaze direction may be defined by a vector in space pointing at the object the user watches. In other words, the gaze direction may be defined by the gaze point and the position of the foveal region of the retina. According to an embodiment, the first gaze direction and the second gaze direction may be determined based on the gaze point of the eye and the location of the estimated cornea sphere center. Advantageously, the gaze point may be a known point in space, such as e.g. a calibration structure having a known location relative to e.g. the image sensor viewing the eye.

The term pupil size may refer to the size of the pupil as represented in an image of the eye, or to the actual size of the pupil or aperture of the eye as defined by the iris. Other definitions are however also conceivable, such as the size of the imaged pupil when projected onto a sphere representing the curvature of the cornea, or the like. The pupil edge pixels in the image may be employed to estimate the position of the center of the pupil, the edge of the pupil and the pupil size (which for example may be determined in terms of a radius of the pupil).

According to an embodiment, the gaze tracking data associated with the eyes having the first pupil size and the second pupil size, respectively, may be stored in a storage area. The storage area may for example form part of the above described system, or be communicatively connected to, but not included in, the system. By storing the gaze tracking data, such as e.g. images of the eyes, from which the eye direction and pupil size may have been retrieved, these data may be reused in subsequent calibration or later adjustment of the compensation model. The stored data could also be referred to as raw data.

Hence, according to an embodiment, the method may comprise the additional steps of obtaining a further angular offset between a further eye direction and a further gaze direction of the eye having a further pupil size, and updating the compensation model based on the stored gaze tracking data, the further pupil size and the further angular offset.

According to an embodiment, the eye tracking system may comprise at least one illuminator for illuminating the eye, and at least one image sensor, or camera, for capturing images of the eye. The illuminator may for example comprise at least two light sources, such as light emitting diodes, arranged to generate at least two glints on the cornea of the eye. The light emitted by the illuminator may in some examples be infrared or near-infrared light.

According to a third aspect, a device that is adapted to be worn by a user is disclosed. The device may e.g. be a virtual reality headset or a pair of augmented reality glasses. The device may comprise at least one illuminator for illuminating an eye of the user, at least one camera for capturing images of the eye, and a circuitry. The circuitry may be configured to obtain a first angular offset between a first eye direction and a first gaze direction of the eye having a first pupil size, obtain a second angular offset between a second eye direction and a second gaze direction of the eye having a second pupil size, and form, based on the first angular offset and the second angular offset, a compensation model describing an estimated angular offset as a function of pupil size.

Embodiments of the method of the first aspect may be performed by the system of any of the embodiments of the second aspect, or by the device of the third aspect, or by the circuitry comprised in such systems/devices.

According to a fourth aspect, a computer program product is disclosed, comprising one or more computer-executable instructions that, when executed by a computing system that implements eye/gaze data processing, cause the computing system to perform a method. The method may for example be the method according to the first aspect.

Embodiments of the one or more computer-readable storage media according to the third aspect may for example include features corresponding to the features of any of the embodiments of the system according to the second aspect or the device according to the third aspect.

The one or more computer-readable media may for example be one or more non-transitory computer-readable media.

It is noted that embodiments of the invention relate to all possible combinations of features recited in the claims.

The above, as well as additional objects, features and advantages of the present invention, will be better understood through the following illustrative and non-limiting detailed description, with reference to the appended drawings. In the drawings like reference numerals will be used for like elements unless stated otherwise.

FIG. 1 shows an eye tracking system 100 (which may also be referred to as a gaze tracking system), according to an embodiment. The system 100 may comprise illuminators 111, 112 for illuminating an eye of a user, and an image sensor 113 (which also may be referred to as a light sensor) for capturing images of the eye of the user. The illuminators 111, 112 may for example be light emitting diodes emitting light in the infrared frequency band, or in the near infrared frequency band. The light sensor 113 may for example be a camera, such as a complementary metal oxide semiconductor (CMOS) camera or a charged coupled device (CCD) camera.

A first illuminator 111 may be arranged coaxially with (or close to) the image sensor 113 so that the image sensor 113 may capture bright pupil images of the user's eye. Due to the coaxial arrangement of the first illuminator 111 and the image sensor 113, light reflected from the retina of the eye returns back out through the pupil towards the image sensor 113, so that the pupil may appear brighter than the iris surrounding it in images where the first illuminator 111 illuminates the eye. A second illuminator 112 may be arranged non-coaxially with (or further away from) the image sensor 113 for capturing dark pupil images. Due to the non-coaxial arrangement of the second illuminator 112 and the image sensor 113, light reflected from the retina of the eye does not reach the image sensor 113 and the pupil may appear darker than the iris surrounding it in images where the second illuminator 112 illuminates the eye. The illuminators 111 and 112 may for example take turns to illuminate the eye, so that every second image is a bright pupil image, and every second image is a dark pupil image.

The eye tracking system 100 may also comprise circuitry 120 (for example including one or more processors) for processing the images captured by the image sensor 113. The circuitry 120 may for example be connected to the image sensor 113 and the illuminators 111, 112 via a wired or a wireless connection. In another example, circuitry 120 in the form of one or more processors may be provided on one or more stacked layers below the light sensitive surface of the image sensor 113.

Figure 2:
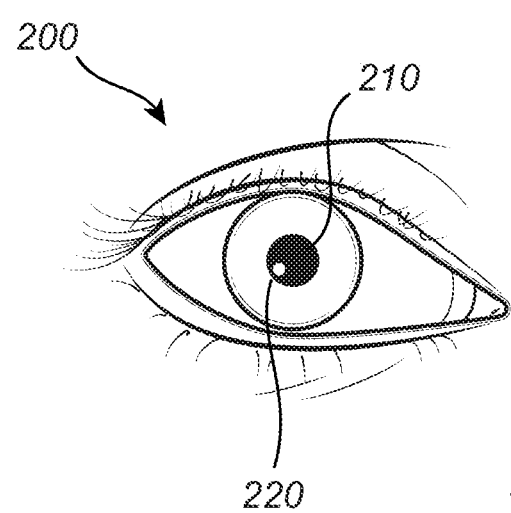
FIG. 2 shows an example image of an eye.

FIG. 2 shows an example of an image of an eye 200, captured by the image sensor 113 as discussed in connection with the system 100 of FIG. 1. The circuitry 120 may for example employ image processing (such as digital image processing) for extracting features in the image. The circuitry 120 may for example be configured to estimate a size of the pupil 210, e.g. in terms of a radius, and the position of a center of the pupil. The circuitry 120 may further be configured to estimate the position of the center of the glints 120 caused by reflection of light from the illuminators 111, 112, and from these positions calculate wherein the user's eye 200 is pointing. Since there is typically an offset between the optical center of the eye 200 and the fovea, the processor performs calibration of the fovea offset to be able to determine where the user is looking. This will be described in more detail with reference to FIGS. 3 and 4.

In the embodiments described with reference to FIGS. 1 and 2, the illuminators 111, 112 may be arranged in an eye tracking module 110 placed below a display watched by the user. This arrangement serves only as an example. It will be appreciated that more or less any number of illuminators and image sensors may be employed for eye tracking, and that such illuminators and image sensors may be distributed in many different ways relative to the user and any scenes or displays watched by the user. It will be appreciated that the eye tracking scheme described in the present disclosure may for example be employed for remote eye tracking (for example in a personal computer, a smart phone, or integrated in a vehicle) or for wearable eye tracking (such as in virtual reality glasses or augmented reality glasses).

Figure 3:
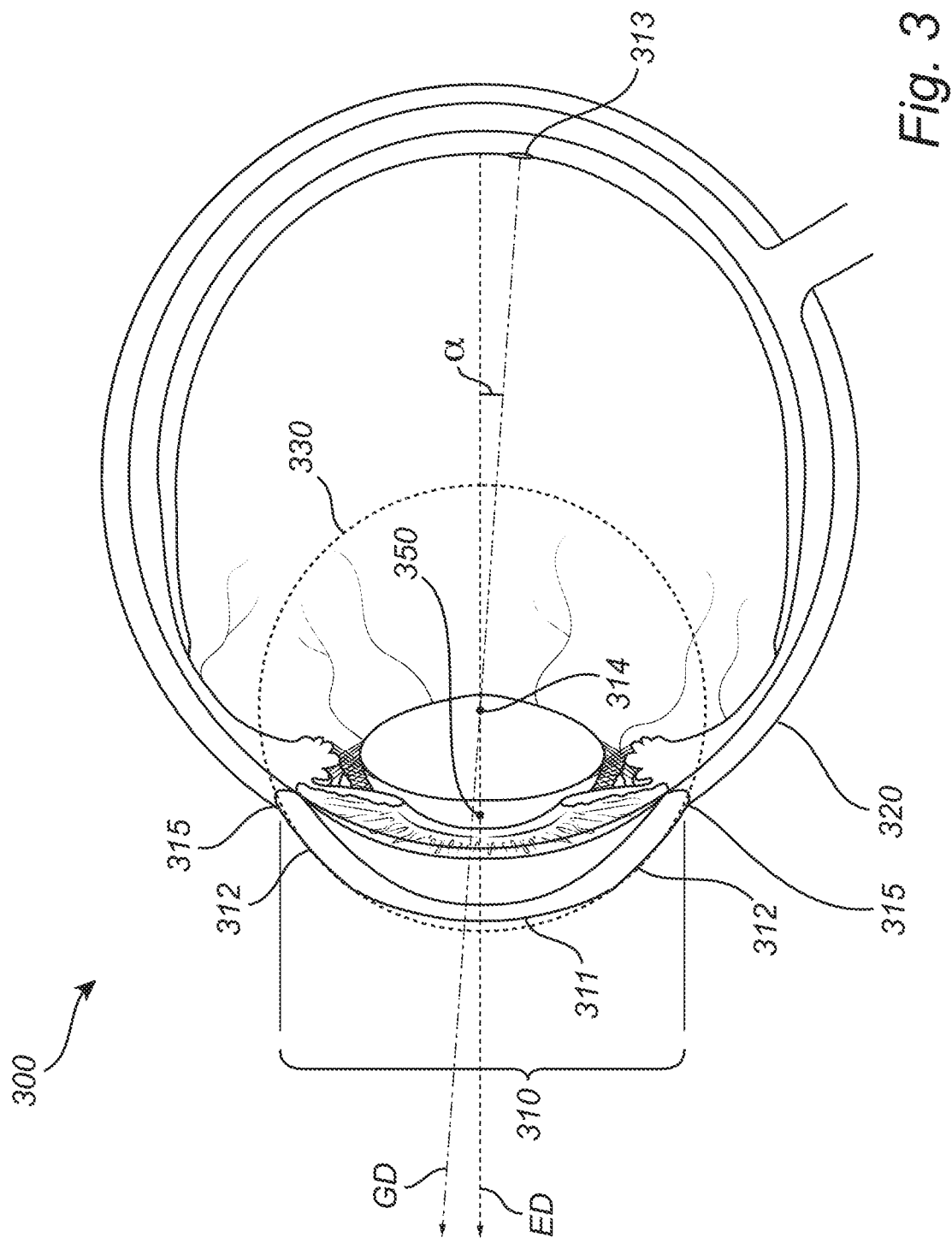
FIG. 3 is a cross sectional view of a part of an eye.

An example of how to determine the eye direction and the angular offset between the eye direction and the gaze direction will now be described with reference to FIG. 3. FIG. 3 shows a cross section of different parts of an eye 300. The cornea 310 has a central region 311 which in general may have a three-dimensional curvature that may be close to spherical, and an outer region 312 which may be less spherical. The cornea 310 may therefore be approximated with a surface portion of sphere 330 (illustrated by a dashed line in the present figure), having an estimated three-dimensional center point 314 located within the eye. In other words, at least a part of the cornea surface of the eye may be approximated with a shape that can be inscribed in, or conform with, a surface portion of an imaginary sphere 330. The center point may also be referred to as the cornea sphere center 314, and may be calculated from the position of the glints 220 on the cornea surface. The cornea sphere center 314 and the estimated location of the pupil center 350 (also determined from image data) define the optical axis, also referred to as the eye direction ED, of the eye 300. As illustrated in FIG. 3, the optical axis ED may extend from the retina through the cornea sphere center 314, the pupil center 350 and the cornea. As the optical axis may be derived from the estimated cornea sphere center 314 and the pupil center 350, it may also vary as the location of the pupil center 350 varies.

Meanwhile, the visual axis, also referred to as the gaze direction GD, extends from the fovea 313, through the cornea sphere center 314. The visual axis may thus be determined by the physical location of the foveal part of the retina and the configuration of the cornea, and may therefore be less sensitive to variations of the pupil size and location. The orientation of the visual axis, or gaze direction GD, may be determined during calibration of the system, when the user watches a point of gaze having a known position.

As depicted, the visual axis GD may deviate from the optical axis ED by an angular offset α. This offset may be determined by means of a calibration process, in which the known gaze direction GD is compared to the eye direction ED. Even though the illustrated example shows an angular offset in the plane of the paper, it will be realized that the offset also may be oriented in a direction normal to that plane, or in any combinations thereof. Hence, the angular offset α between the eye direction ED and the gaze direction GD may be represented by a vector indicating the offset for example in the medial-lateral and the cranial-caudal directions of the eyeball.

Figure 4A:
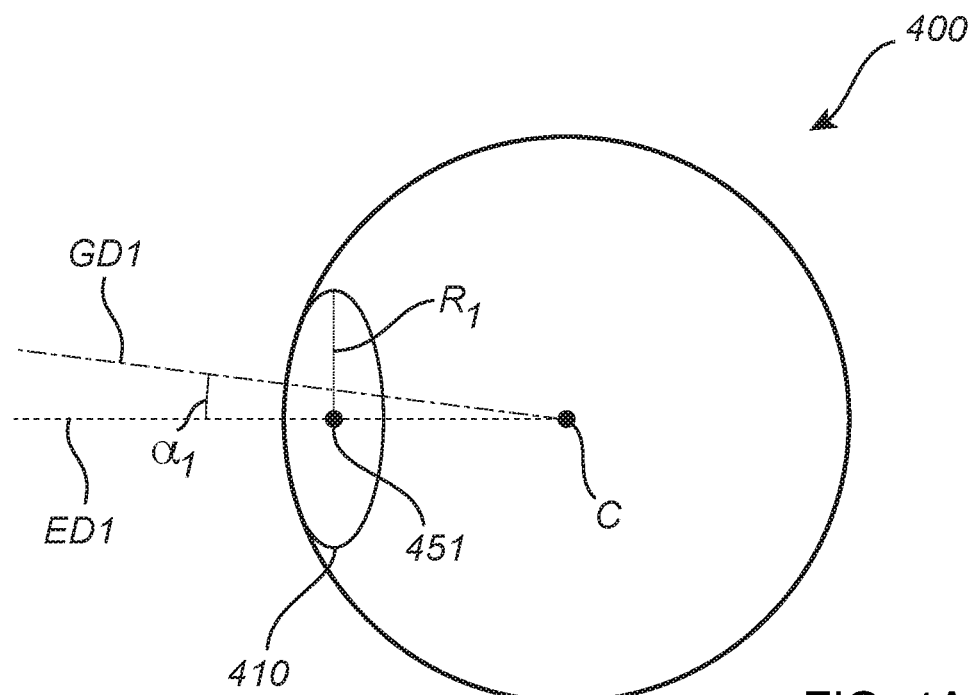
FIGS. 4A and 4B are perspective views of an eye having a first pupil size, and the eye having a second pupil size.
Figure 4B:
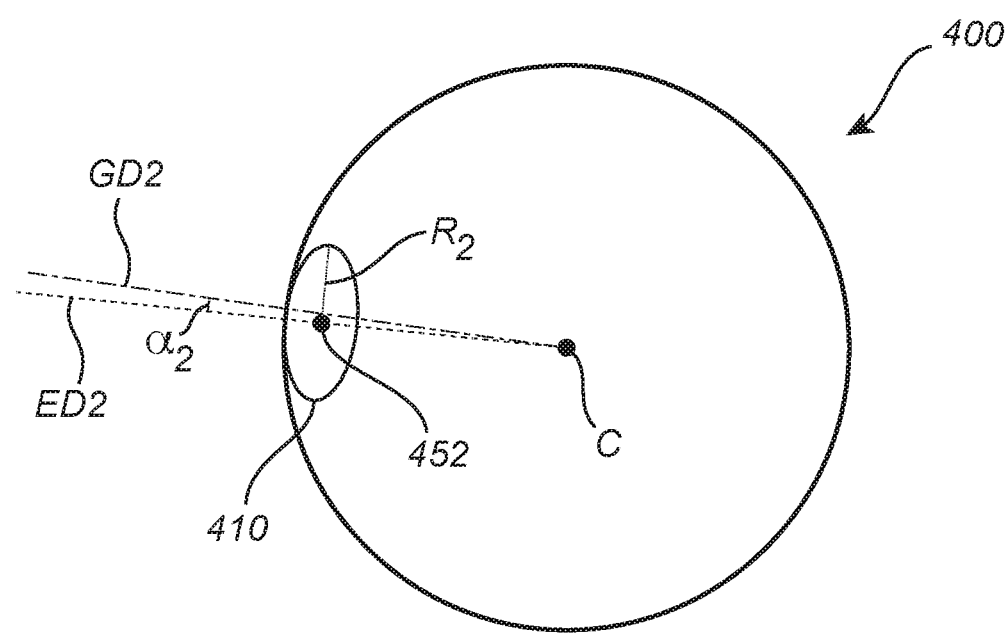

FIG. 4A shows perspective views of an eye 400 wherein the pupil 410 has a first size, or radius, R1. FIG. 4B is a perspective view of the same eye 400 having a second pupil size R2. The pupil size may for example vary with the illumination intensity, where an increase in intensity is known to cause the iris 410 to constrict and a reduction in intensity may cause the iris 420 to dilate. This is a known effect for applications in which the eye is exposed to for example ambient lighting, such as augmented reality applications, or a dynamic display brightness.

The location of the pupil center 451, 452 may shift with the change in pupil size, which thereby may affect the estimated eye direction ED and hence the angular offset used for calculating the gaze direction GD. In the present figures, the shift in the medial/lateral position of the pupil center of the eye is indicated by the angular offset $\alpha_1$, $\alpha_2$, suggesting that the pupil center in the present example is shifted upwards (in the cranial direction) relative to a center point c of the eye as the pupil size is reduced from the first size R1 to the second size R2.

In FIG. 4A the eye 400 has a first, dilated pupil size R1, with the first angular offset cu between the first eye direction ED1 and the first gaze direction GD1. If the location of the pupil center 451 is shifted, for example due to a constriction of the iris 410, the estimated eye direction ED1 may change as illustrated in FIG. 4B, which shows the eye 400 having a second, constricted pupil size R2 resulting in a second angular offset $\alpha_2$ between the second eye direction ED2 and the second gaze direction GD2. It will be noted that the first and the second eye direction ED1, ED2 therefore may differ from each other due to the shift in pupil center position, whereas the first and second gaze direction GD1, GD2 (which in this example by be defined by the center point c) may be less affected by the shift in pupil position. In some examples, the gaze direction GD1, GD2 may be assumed to be the same for both pupil sizes R1, R2.

Hence, the shift of the pupil center location 451, 452 may result in a change in angular offset from a first angular offset $\alpha_1$ to a second angular offset $\alpha_2$. This relation allows for the angular offset $\alpha_1$, $\alpha_2$ to be mapped against different pupil sizes R1, R2 during for example a calibration of the system, i.e., when the user watches a point in space having a known location. Based on this information, a compensation model may be formed which describes the estimated angular offset as a function of the pupil size. Alternatively, or additionally, the illumination intensity may be linked to the angular offset $\alpha_1$, $\alpha_2$ to form a similar model of the offset as a function of the illumination intensity. Preferably, such model should be calibrated to each individual user, as the iris of different users may be assumed to react differently on different illumination intensities.

In one example, the angular offset $\alpha$ for a specific pupil size may be estimated by a linear approximation. Put differently, the angular offset may be described by the following expression:

$$\alpha(R) = kR + m$$

where $\alpha$ is the angular offset between the gaze direction GD and the eye direction ED, R is the pupil radius (preferably obtained from an image of the eye) and k and m are constants set for example during calibration. The model may be determined based on at least two measured points, e.g., a first and a second pupil size and a corresponding first and second angular offset value. It will however be appreciated that the current invention by no means is limited to linear approximations based on two measurements. Other models, such as higher order polynomial approximations may be used together with a data sets comprising three or more different pupil sizes and angular offsets. The following mathematical relation is an example of a higher order polynomial model:

$$\alpha(R) = \sum_{i=0}^{i=n} a_i R^i$$

were R is the pupil radius, n the polynomial degree (or order) and a the parameter set determined during the calibration.

Figure 5:
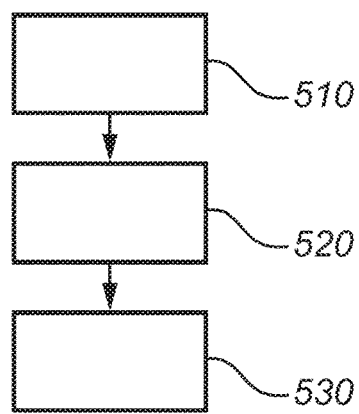
FIGS. 5-7 are flow charts of methods according to embodiments of the invention.

FIG. 5 is a flow chart of a method according to an embodiment of the present invention. The method may for example be performed by the eye tracking system 100 described above with reference to FIG. 1, or the circuitry 120 comprised in the eye tracking system 100.

The method comprises obtaining 510 a first angular offset $\alpha_1$ between a first eye direction ED1 and a first gaze direction GD1 of an eye 300 having a first pupil size R1, obtaining 520 a second angular offset $\alpha_2$ between a second eye direction ED2 and a second gaze direction GD2 of the eye 300 having a second pupil size R2, and forming 530, based on the first angular offset $\alpha_1$ and the second angular offset $\alpha_2$, a compensation model describing an estimated angular offset $\alpha$ as a function of pupil size R.

One or several of the above steps 510, 520, 530 may be performed by the circuitry 120 of the eye tracking system 100. It will be appreciated that the circuitry 120 may be integrated in a single unit, or distributed between several physically distinct units that may be arranged at different locations. Thus, according to an example, the first and second angular offsets $\alpha_1$, $\alpha_2$ may be obtained at a first circuitry unit, and then transmitted to a second circuitry unit at which the data are processed to form the compensation model.

The first and second angular offsets $\alpha_1$, $\alpha_2$ may be obtained from gaze tracking data for the eye 300, which in turn may be retrieved from an image of the eye 300. The gaze tracking data may e.g. comprise information from which the pupil center 350, the pupil size (such as e.g. radius or diameter) R, and the cornea center 314 may be derived—preferably, but not necessarily—in a similar manner as described for example in connection with FIGS. 3a and *b*. These images may for example be obtained from an image sensor, such as a camera, as disclosed in connection with FIG. 1. The image sensor may be arranged to capture images of the eye 300 reflecting glints from one or several illuminators 111, 112. The images may be captured at different illumination intensities, for example at different ambient light conditions, so as to obtain information representing different pupil sizes R1, R2. In one example, the images may be obtained during a calibration procedure in which the user watches known positions on for example a display. The calibration procedure may for example be a nine-point calibration procedure, in which the eye(s) of the user is/are captured when the user watches each one of nine physically separate points on the display.

Figure 6:
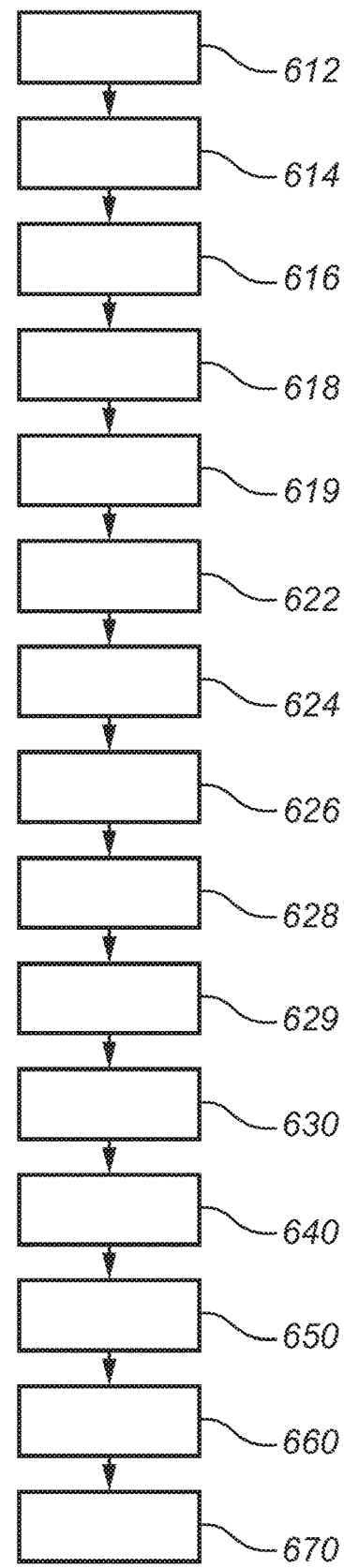

FIG. 6 is a flow chart of a method according to an embodiment, which may be similar to the method according to the embodiment described with reference to FIG. 5. In the present embodiment, a first image may be acquired 612, e.g. by a image sensor of a system according to an embodiment similar to the one discussed above in connection with FIG. 1, of the eye having a first pupil size R1. The captured image may be analyzed in order to determine 614 the first eye direction ED1 based on the location of the estimated cornea sphere center 314 and the location of the estimated pupil center 350, and to determine 616 the first gaze direction GD1 based on a known point of gaze (for example obtained from a calibration pattern) and the estimated cornea sphere center 314. Further, the pupil size R1 may be determined 618 from the same image. The first gaze direction GD1 and the first eye direction ED1 may then be used to determine 619 (e.g. by means of a processor or circuitry) the angular offset $\alpha_1$ between the two directions, and to associate the angular offset $\alpha_1$ with the specific pupil size R1 the eye when the image was captured.

The above steps 612-619 may be repeated for a second image of the eye, preferably having a second pupil size R2 differing from the first pupil size R1. Thus, the method may comprise the steps of acquiring 622 a second image of the eye, analyzing the second image to determine 624 the second eye direction ED2 based on the location of the estimated cornea sphere center 314 (this location may either be determined based on the second image, or retrieved from a prior measurement, such as e.g. the first image or previously stored calibration data), and the location of the estimated pupil center 350 (which may be assumed to differ from the estimated pupil center of the first image, given that the pupil radius varies between the two images). Further, the method may comprise the steps of determining 626 the second gaze direction GD2 based on a known point of gaze (which may be the same point as for the first image, or a different point in space) and the estimated cornea sphere center 314. The angular offset $\alpha2$ between the second gaze direction GD2 and the second eye direction ED2 may then be determined 629 and associated with the second pupil size R2, which may be determined 628 from the same image.

The first angular offset $\alpha1$, the second angular offset $\alpha2$, and the respective pupil sizes R1, R2 may in a subsequent step be used for forming 630 the compensation model describing the angular offset $\alpha$ as a function of the pupil size R. The model may for example be a linear model, a polynomial approximation or an s-curve, or a set of entries of a lookup-table. The model may be stored 640 in a storage area of the system, or sent to a storage area to which the system (or circuitry) has access. The storage area may further be adapted to store 650 the images used for obtaining the angular offsets during the calibration procedure, or storing raw data retrieved from the images, for later use. In case a further angular offset between a further eye direction and a further gaze direction of the eye, having a further pupil size, is obtained 660 from a further image of the eye, this further angular offset may be employed to update 670 the compensation model based on the previously stored raw data, the further pupil size and the further angular offset.

Thus, it will be appreciated that the present inventive concept is not limited to methods wherein only two images are used for determining angular offsets, pupil radii and the compensation model. On the contrary, the compensation model may be formed based on eye tracking data obtained from three or more images, and may further be dynamically updated during use of the eye tracking system.

Figure 7:
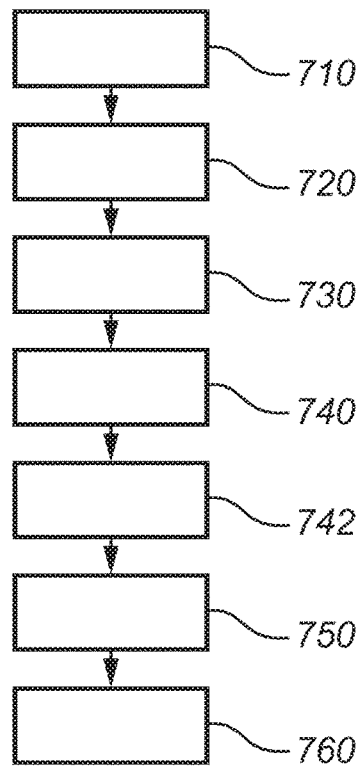

FIG. 7 is a flow chart of a method according to an embodiment, which may be similar to the embodiments discussed in connection with the previous FIGS. 5 and 6. Accordingly, the method may comprise the steps of obtaining 710 a first angular offset $\alpha1$ between a first eye direction ED1 and a first gaze direction GD1 of an eye having a first pupil size R1, obtaining 720 a second angular offset $\alpha2$ between a second eye direction ED2 and a second gaze direction GD2 of the eye when the eye has a second pupil size R2, and forming 730, based on the first angular offset $\alpha1$ and the second angular offset $\alpha2$, a compensation model of the estimated angular offset $\alpha$ as a function of the pupil size R for the eye.

In a subsequent part of the method, the compensation model may be employed for tracking the gaze during use. Thus, the method according to the present embodiment may comprise the further steps of obtaining 740 a third eye direction ED3, determining 742 the pupil size R3, and using the compensation model to determine 750 the angular offset $\alpha$ associated with the determined pupil size R3. The angular offset $\alpha$ may then be used for calculating 760 the third gaze direction GD3 of the eye. The above described steps, i.e., the steps of obtaining 740 the third eye direction, determining the pupil size 742, determining the angular offset 750 and applying the offset to the third eye direction ED3 to obtain the third gaze point GD3, may be performed repeatedly so as to achieve an active tracking of the gaze during use of the system.

Figure 8:
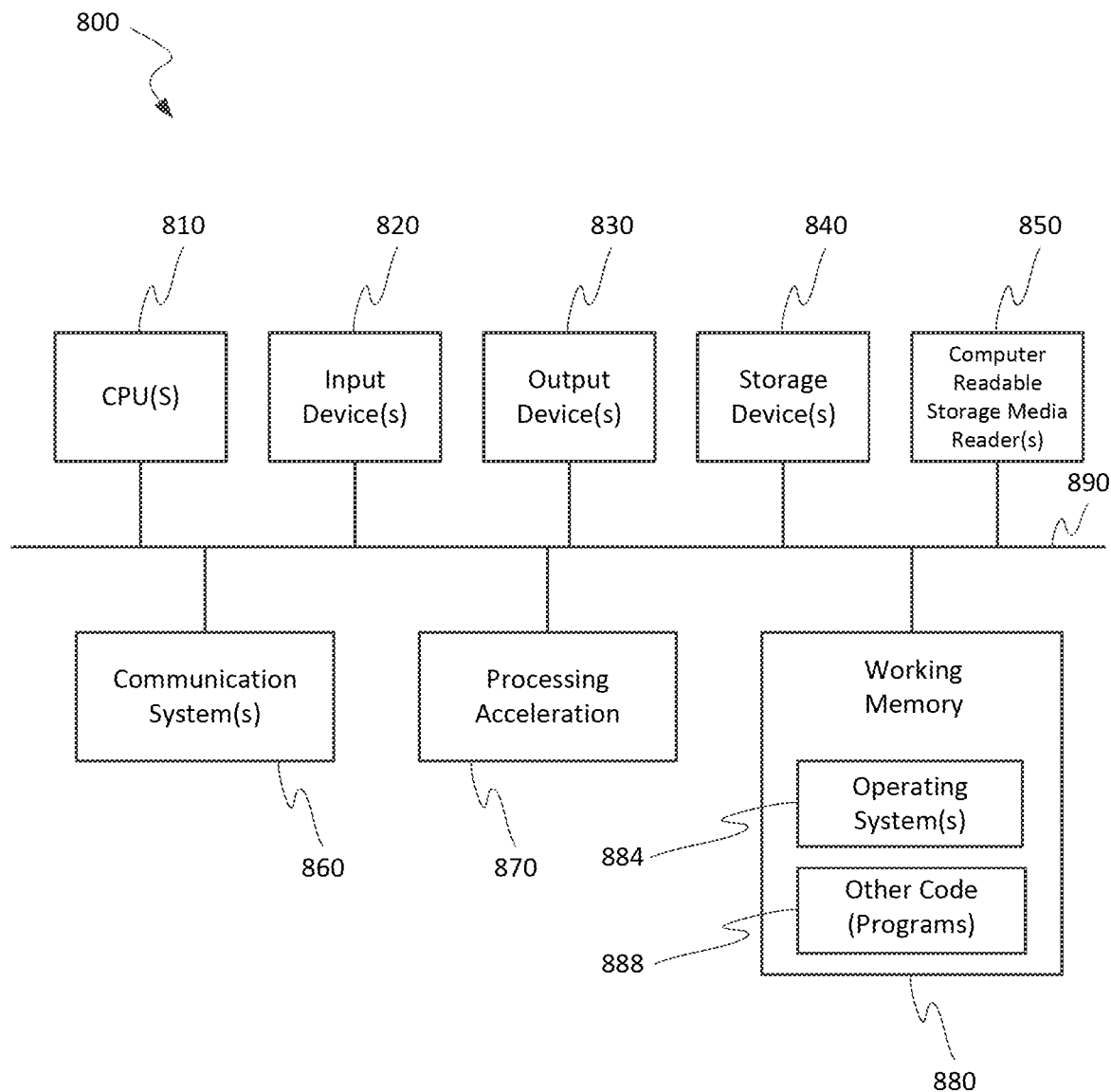
FIG. 8 is a block diagram of a specialized computer system capable of being used in at least some portion of the apparatuses or systems of the present invention, or implementing at least some portion of the methods of the present invention.

FIG. 8 is a block diagram illustrating a specialized computer system 800 in which embodiments of the present invention may be implemented. This example illustrates specialized computer system 800 such as may be used, in whole, in part, or with various modifications, to provide the functions of components described herein.

Specialized computer system 800 is shown comprising hardware elements that may be electrically coupled via a bus 890. The hardware elements may include one or more central processing units 810, one or more input devices 820 (e.g., a mouse, a keyboard, eye tracking device, etc.), and one or more output devices 830 (e.g., a display device, a printer, etc.). Specialized computer system 800 may also include one or more storage device 840. By way of example, storage device(s) 840 may be disk drives, optical storage devices, solid-state storage device such as a random access memory ("RAM") and/or a read-only memory ("ROM"), which can be programmable, flash-updateable and/or the like.

Specialized computer system 800 may additionally include a computer-readable storage media reader 850, a communications system 860 (e.g., a modem, a network card (wireless or wired), an infra-red communication device, Bluetooth™ device, cellular communication device, etc.), and working memory 880, which may include RAM and ROM devices as described above. In some embodiments, specialized computer system 800 may also include a processing acceleration unit 870, which can include a digital signal processor, a special-purpose processor and/or the like.

Computer-readable storage media reader 850 can further be connected to a computer-readable storage medium, together (and, optionally, in combination with storage device(s) 840) comprehensively representing remote, local, fixed, and/or removable storage devices plus storage media for temporarily and/or more permanently containing computer-readable information. Communications system 860 may permit data to be exchanged with a network, system, computer and/or other component described above.

Specialized computer system 800 may also comprise software elements, shown as being currently located within a working memory 880, including an operating system 884 and/or other code 888. It should be appreciated that alternate embodiments of specialized computer system 800 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of specialized computer system 800 may include code 888 for implementing any or all of the function of the various elements of the architecture as described herein. For example, software, stored on and/or executed by a specialized computer system such as specialized computer system 800, can provide the functions of components of the invention such as those discussed above. Methods implementable by software on some of these components have been discussed above in more detail.

The person skilled in the art realizes that the present invention is by no means limited to the preferred embodiments described above. On the contrary, may modifications and variations are possible within the scope of the appended claims. For example, the person skilled in the art realizes that the eye/gaze tracking methods described herein may be performed by many other eye/gaze tracking systems than the eye/gaze tracking system 100 shown in FIG. 1, for example using multiple illuminators and multiple cameras.

Additionally, variation to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The division of tasks between functional units referred to in the present disclosure does not necessarily correspond to the division into physically distinct units; to the contrary, a physical component may have multiple functionalities, and a task may be carried out in a distributed fashion, by several physical components in cooperation. A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

The mere fact that certain measures/features are recited in mutually different dependent claims does not indicate that a combination of these measures/features cannot be used to advantage. Method steps need not necessarily be performed in the order in which they appear in the claim or in the embodiments described herein, unless it is explicitly described that a certain order is required. Any reference signs in the claims should not be construed as limiting the scope.

What is claimed is:

1. A method comprising:
   obtaining a first angular offset between a first eye direction and a first gaze direction of an eye having a first pupil size;
   obtaining a second angular offset between a second eye direction and a second gaze direction of the eye having a second pupil size; and
   forming, based on the first angular offset and the second angular offset, a compensation model describing an estimated angular offset as a function of pupil size,
   obtaining a third eye direction of the eye having a third pupil size;
   determining, based on the compensation model, an estimated angular offset associated with the third pupil size; and
   determining, based on the third eye direction and the estimated angular offset associated with the third pupil size, a third gaze direction of the eye.

2. The method according to claim 1, wherein:
   the first eye direction and the first pupil size are obtained from a first image of the eye having the first pupil size; and
   the second eye direction and the second pupil size are obtained from a second image of the eye having the second pupil size.

3. The method according to claim 2, further comprising acquiring the first image of the eye and acquiring the second image of the eye.

4. The method according to claim 3, wherein the first image is acquired at a first illumination intensity and the second image is acquired at a second illumination intensity, differing from the first illumination intensity.

5. The method according to claim 1, wherein the first eye direction and the second eye direction are determined based on a location of an estimated cornea sphere center and a location of an estimated pupil center of the eye having the first and second pupil size, respectively.

6. The method according to claim 1, wherein the first gaze direction and the second gaze direction are determined based on a location of an estimated cornea sphere center and a point of gaze of the eye having the first and second pupil size, respectively.

7. The method according to claim 1, comprising:
   determining, based on an image of the eye having the first pupil size and an image of the eye having the second pupil size, the actual size of the respective pupil.

8. The method according to claim 1, comprising:
   storing gaze tracking data associated with the eye having the first pupil size and the second pupil size.

9. The method according to claim 8, comprising:
   obtaining a further angular offset between a further eye direction and a further gaze direction of the eye having a further pupil size;
   updating the compensation model based on the stored gaze tracking data, the further pupil size and the further angular offset.

10. A computer program product comprising one or more computer-readable media with instructions for performing the method of claim 1.

11. An eye tracking system comprising a circuitry configured to:
    obtain a first angular offset between a first eye direction and a first gaze direction of an eye having a first pupil size;
    obtain a second angular offset between a second eye direction and a second gaze direction of the eye having a second pupil size; and
    form, based on the first angular offset and the second angular offset, a compensation model describing an estimated angular offset as a function of pupil size,
    determine the first eye direction and the first pupil size from a first image of the eye; and
    determine the second eye direction and the second pupil size from a second image of the eye,
    obtain a third eye direction of the eye having a third pupil size;
    determine, based on the compensation model, an estimated angular offset associated with the third pupil size; and
    determine, based on the third eye direction and the estimated angular offset associated with the third pupil size, a third gaze direction of the eye.

12. The eye tracking system according to claim 11, wherein the circuitry is configured to:
    determine the first eye direction and the second direction based on a location of an estimated cornea sphere center and a location of an estimated pupil center of the eye having the first and second pupil size, respectively.

13. The eye tracking system according to claim 11, wherein the circuitry is configured to:
  determine the first gaze direction and the second gaze direction based on a location of an estimated cornea sphere center and a point of gaze of the eye having the first and second pupil size, respectively.

14. The eye tracking system according to claim 11, comprising:
  at least one illuminator for illuminating the eye; and
  at least one camera for capturing images of the eye.

15. The eye tracking system according to claim 14, wherein said at least one illuminator is configured to emit infrared or near-infrared light.

16. The eye tracking system according to claim 11, wherein the circuitry has its disposal a storage area configured to store data representing the compensation model.

17. A device adapted to be worn by a user, comprising:
  at least one illuminator for illuminating an eye of the user;
  at least one camera for capturing images of the eye;
  a circuitry configured to:
  obtain a first angular offset between a first eye direction and a first gaze direction of the eye having a first pupil size;
  obtain a second angular offset between a second eye direction and a second gaze direction of the eye having a second pupil size; and
  form, based on the first angular offset and the second angular offset, a compensation model describing an estimated angular offset as a function of pupil size,
  obtain a third eye direction of the eye having a third pupil size;
  determine, based on the compensation model, an estimated angular offset associated with the third pupil size; and
  determine, based on the third eye direction and the estimated angular offset associated with the third pupil size, a third gaze direction of the eye.

* * * * *